US011029280B2

(12) United States Patent
Kroll et al.

(10) Patent No.: US 11,029,280 B2
(45) Date of Patent: Jun. 8, 2021

(54) ALKALINITY SENSOR

(71) Applicant: HACH COMPANY, Loveland, CO (US)

(72) Inventors: Dan Kroll, Fort Collins, CO (US); Corey Salzer, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 110 days.

(21) Appl. No.: 15/745,586

(22) PCT Filed: Jun. 22, 2017

(86) PCT No.: PCT/US2017/038842
§ 371 (c)(1),
(2) Date: Jan. 17, 2018

(87) PCT Pub. No.: WO2017/223365
PCT Pub. Date: Dec. 28, 2017

(65) Prior Publication Data
US 2018/0224397 A1 Aug. 9, 2018

Related U.S. Application Data

(60) Provisional application No. 62/354,017, filed on Jun. 23, 2016.

(51) Int. Cl.
*G01N 27/44* (2006.01)
*G01N 27/30* (2006.01)
(Continued)

(52) U.S. Cl.
CPC .......... *G01N 27/44* (2013.01); *G01N 27/302* (2013.01); *G01N 27/308* (2013.01);
(Continued)

(58) Field of Classification Search
CPC ... G01N 31/164; G01N 27/44; G01N 27/4167
See application file for complete search history.

(56) References Cited

U.S. PATENT DOCUMENTS 2,192,123 A * 2/1940 Bennett .............. G01N 27/4167
205/787.5
5,230,785 A * 7/1993 Yager ................... G01N 33/182
204/400
(Continued)

FOREIGN PATENT DOCUMENTS

GB 2518263 * 3/2015 ............. G01N 27/30

*Primary Examiner* — Luan V Van
*Assistant Examiner* — Caitlyn Mingyun Sun
(74) *Attorney, Agent, or Firm* — Ference & Associates LLC

(57) ABSTRACT

An embodiment provides a method for determining the alkalinity of an aqueous sample using an alkalinity sensor, including: monitoring the pH of an aqueous sample using a pH sensor in a sample cell, the pH sensor including a pH sensor electrode made of boron-doped diamond; generating hydronium ions, using a hydronium generator, in the aqueous sample in the sample cell, the hydronium generator including a hydronium-generating electrode; changing the pH of the aqueous sample by causing the hydronium generator to generate an amount of hydronium ions in the aqueous sample; quantifying and converting a current or charge to the number of hydronium ions produced to an end point of the electrochemical titration, the end point correlating to the alkalinity of a sample; and analyzing the alkalinity of the aqueous sample based on the generated amount of hydronium ions and the resulting change in pH monitored by the pH sensor.

9 Claims, 13 Drawing Sheets

| # | Legend Description |
|---|---|
| 1 | Switch to alternate between hydronium ion generator and pH sensor |
| 2 | Inlet for the sample to enter into the analyzers cell |
| 3 | pH measuring electrode |
| 4 | Reference electrode (Ag/AgCl or SCE) |
| 5 | Platinum counter electrode |
| 6 | Reservoir to accommodate Reference and Counter electrode |
| 7 | Outlet for the sample to exit after analysis |
| 8 | Conduit to provide liquid connection between the working electrode and Counter/Refernce electrode compartments |
| 9 | Compartment where hydronium ion generator and pH measuremet occurs |
| 10 | BDD electrode for protonation |
| 11 | Brass plate for providing electrical connection for the BDD protonator |
| 12 | BDD electyrode for pH measurement |
| 13 | First Cell Housing |
| 14 | Second Cell Housing |
| 15 | Peristaltic pump |

(51) Int. Cl.
*G01N 27/416* (2006.01)
*G01N 31/16* (2006.01)
*G01N 33/18* (2006.01)
*G01N 27/42* (2006.01)

(52) U.S. Cl.
CPC ....... *G01N 27/4167* (2013.01); *G01N 27/423* (2013.01); *G01N 31/164* (2013.01); *G01N 33/182* (2013.01)

(56) References Cited

U.S. PATENT DOCUMENTS

| | | | | |
|---|---|---|---|---|
| 5,489,515 | A * | 2/1996 | Hatschek | G01N 27/4167 204/403.01 |
| 8,440,093 | B1 * | 5/2013 | Nassef | G01N 15/1031 216/84 |
| 8,475,639 | B2 * | 7/2013 | Srinivasan | G01N 31/164 204/405 |
| 8,877,037 | B2 * | 11/2014 | Duimstra | G01N 27/36 205/789 |
| 2015/0276662 | A1 * | 10/2015 | Horkheimer | G01N 27/4167 205/789 |

\* cited by examiner

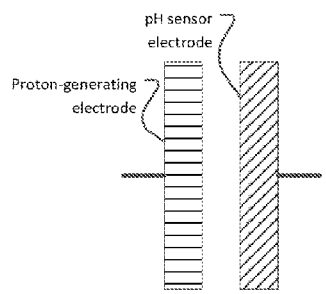
FIG. 4A
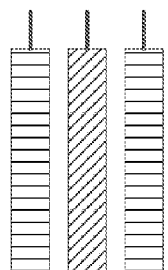
FIG. 4B
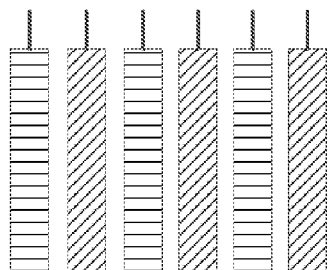
FIG. 4C
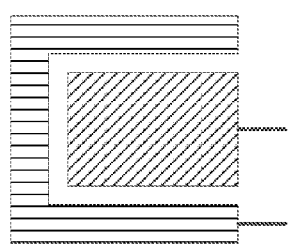
FIG. 4D
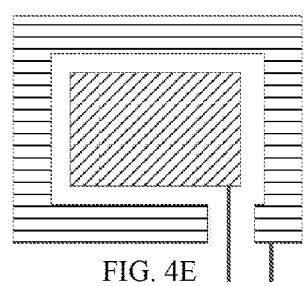
FIG. 4E
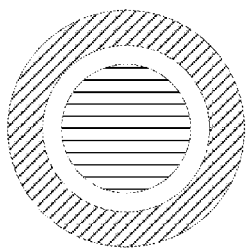
FIG. 4F
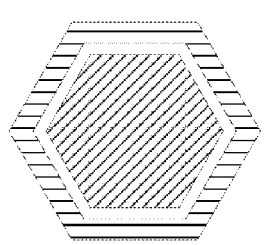
FIG. 4G
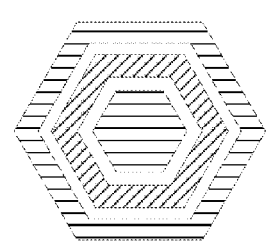
FIG. 4H
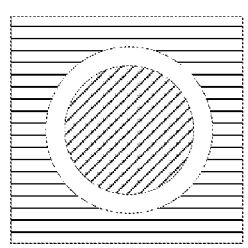
FIG. 4I
FIG. 4

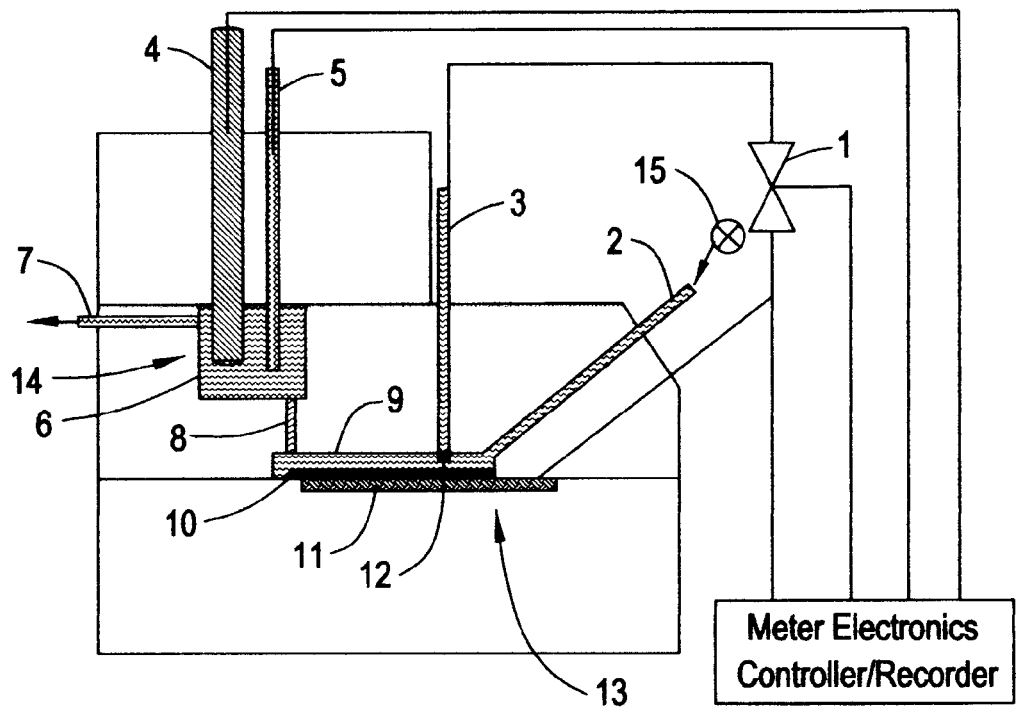

| # | Legend Description |
|---|---|
| 1 | Switch to alternate between hydronium ion generator and pH sensor |
| 2 | Inlet for the sample to enter into the analyzers cell |
| 3 | pH measuring electrode |
| 4 | Reference electrode (Ag/AgCl or SCE) |
| 5 | Platinum counter electrode |
| 6 | Reservoir to accommodate Reference and Counter electrode |
| 7 | Outlet for the sample to exit after analysis |
| 8 | Conduit to provide liquid connection between the working electrode and Counter/Refernce electrode compartments |
| 9 | Compartment where hydronium ion generator and pH measuremet occurs |
| 10 | BDD electrode for protonation |
| 11 | Brass plate for providing electrical connection for the BDD protonator |
| 12 | BDD electyrode for pH measurement |
| 13 | First Cell Housing |
| 14 | Second Cell Housing |
| 15 | Peristaltic pump |

FIG. 7

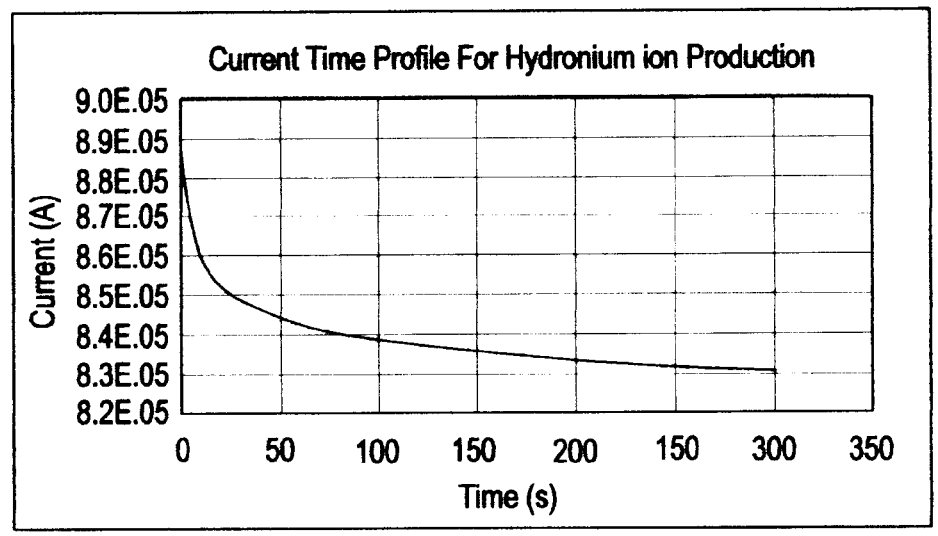
FIG. 9A
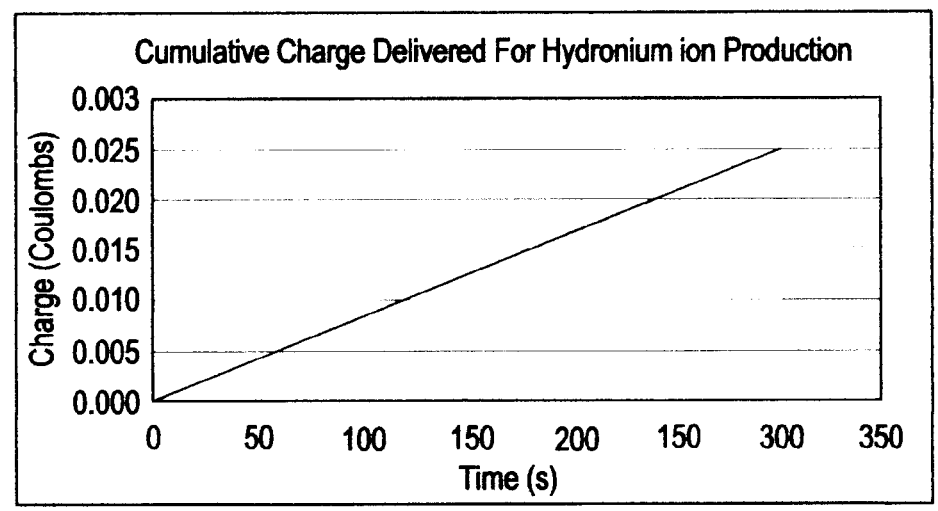
FIG. 9B
FIG. 9

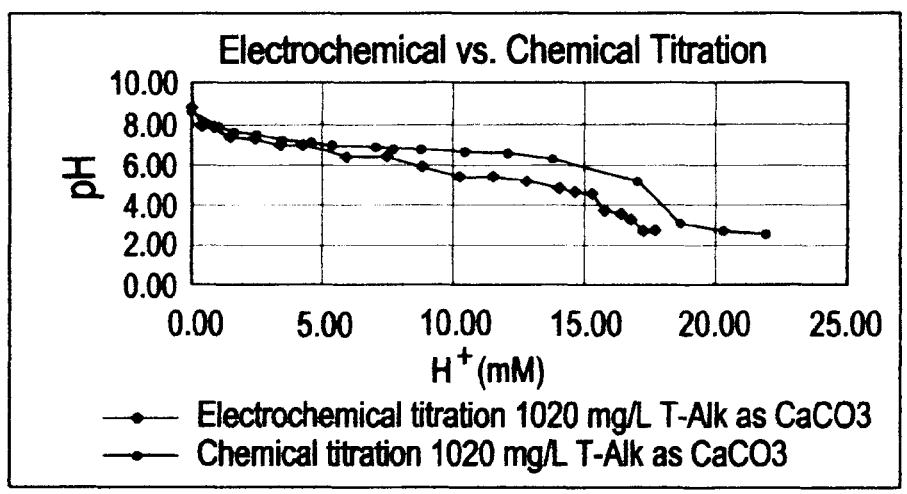
FIG. 14A
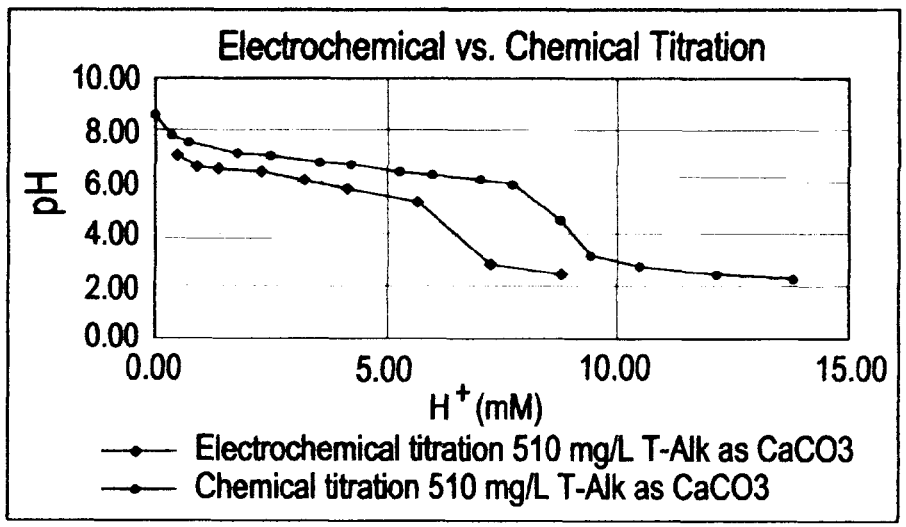
FIG. 14B
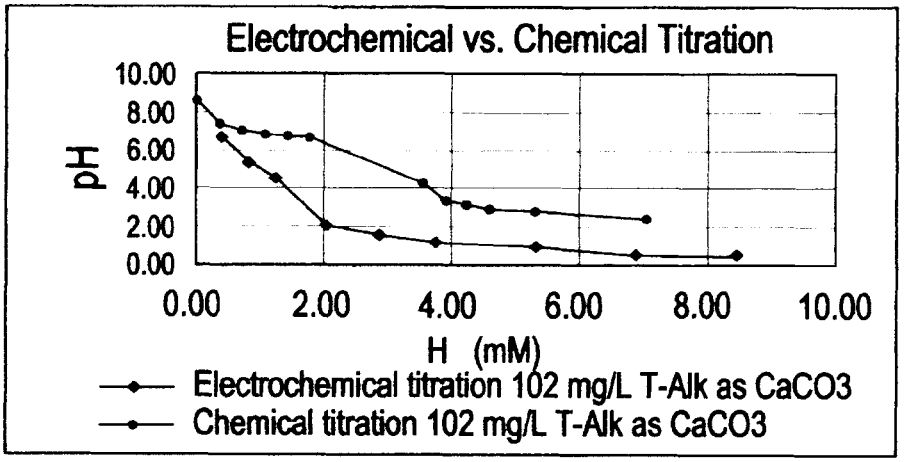
FIG. 14C
FIG. 14

ALKALINITY SENSOR

BACKGROUND

This application relates generally to pH measurement in aqueous samples and, more particularly, to the measurement of the alkalinity present in said samples.

Alkalinity refers to the capability of water to neutralize acid. It is measured by the sum of the titrate-able bases present in the sample. Alkalinity of water is often due to the presence of hydroxides, carbonates, and bicarbonates. Others species such as borate, silicates and phosphates may also contribute to alkalinity. Alkalinity used in this regard is an expression of a water's buffering capacity. A buffered solution is a solution in which acid or base can be added without changing the pH appreciably.

Accurate alkalinity determinations are critical to many industries and water types. Alkalinity is a key parameter that is important in determining chemical dosing levels as well as an indicator of corrosion or fouling. High alkalinity in drinking water can result in an objectionable taste. The measurement of alkalinity is an important commonly analyzed parameter in source water, distribution systems, the power industry, aquaculture, pool and spa, boiler and cooler, wastewater and elsewhere.

Traditionally, alkalinity is determined by titration using a strong acid (i.e., sulfuric acid) to a specific pH using colorimetric or potentiometric endpoint detection. Alkalinity P is determined by titration to an endpoint pH of 8.3. Phenolphthalein is commonly used to obtain this endpoint in a colorimetric titration. Alkalinity P measures total hydroxide and one half of the carbonate present. Alkalinity T (Total) is determined by a further titration to the endpoint of pH 4.5. Total alkalinity is a measure of all carbonates, bicarbonates, hydroxides and may include contribution by phosphates and silicates as well as other contributing elements.

BRIEF SUMMARY

One embodiment provides a method for determining the alkalinity of an aqueous sample using an alkalinity sensor, comprising: monitoring the pH of an aqueous sample using a pH sensor in a sample cell, the pH sensor including a pH sensor electrode made of boron-doped diamond; generating hydronium ions, using a hydronium generator, in the aqueous sample in the sample cell, the hydronium generator including a hydronium-generating electrode; changing the pH of the aqueous sample by causing the hydronium generator to generate an amount of hydronium ions in the aqueous sample; quantifying and converting a current or charge to the number of hydronium ions produced to an end point of the electrochemical titration, the end point correlating to the alkalinity of a sample; and analyzing the alkalinity of the aqueous sample based on the generated amount of hydronium ions and the resulting change in pH monitored by the pH sensor.

Another embodiment provides a system for determining the alkalinity of an aqueous sample, comprising: a processor; a memory device that stores instructions executable by the processor; a bipotentiostat that generates a pH signal indicative of the pH of the aqueous sample and a hydronium generation signal indicative of an amount of hydronium generated in the aqueous sample as a result of electrolysis of water at a hydronium-generating electrode; a controller connected to the bipotentiostat that controls the amount of hydronium ions generated in the aqueous sample; an analyzer that determines the alkalinity of the aqueous sample based on the pH signal and the hydronium generation signal; wherein the bipotentiostat further comprises: a) a pH sensing electrode wired as a first bipotentiostat working electrode, the pH sensing electrode made of boron-doped diamond; b) the hydronium-generating electrode wired as a second bipotentiostat working electrode, the hydronium-generating electrode made of boron-doped diamond; c) at least a first bipotentiostat reference electrode; d) at least a first bipotentiostat counter electrode; and e) a control circuitry connected to the electrodes, the control circuitry adapted to measure and control the voltage difference between the reference electrode and the first and second working electrodes and further adapted to output the pH signal indicative of the pH based on measured first current flow and potential through the first working electrode and the hydronium generation signal indicative of the amount of hydronium ions generated based on measured second current flow through the second working electrode.

A further embodiment provides a product, comprising: a storage device having code stored therewith, the code being executable by the processing and comprising: code that generates, at a bipotentiostat, a pH signal indicative of the pH of the aqueous sample and a hydronium generation signal indicative of an amount of hydronium generated in the aqueous sample as a result of electrolysis of water at a hydronium-generating electrode; code that controls the amount of hydronium ions generated in the aqueous sample; the bipotentiostat further comprising: a) a pH sensing electrode wired as a first bipotentiostat working electrode, the pH sensing electrode made of boron-doped diamond; b) the hydronium-generating electrode wired as a second bipotentiostat working electrode, the hydronium-generating electrode made of boron-doped diamond; c) at least a first bipotentiostat reference electrode; d) at least a first bipotentiostat counter electrode; and e) a control circuitry connected to the electrodes, the control circuitry adapted to measure and control the voltage difference between the reference electrode and the first and second working electrodes and further adapted to output the pH signal indicative of the pH based on measured first current flow and potential through the first working electrode and the hydronium generation signal indicative of the amount of hydronium ions generated based on measured second current flow through the second working electrode; and code that determines the alkalinity of the aqueous sample based on the pH signal and the hydronium generation signal.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

The following drawing figures, which form a part of this application, are illustrative of described technology and are not meant to limit the scope of the disclosure as claimed in any manner, which scope shall be based on the claims appended hereto.

FIGS. 4A-4I illustrates several other pH sensor/hydronium-generating electrode configurations that could be easily obtained with BDD electrodes in an embodiment.

FIG. 7 is a side-view drawing of an electrochemical cell to measure alkalinity in an embodiment.

FIG. 9A-9B Current-time profile for hydronium ion production and the cumulative charge delivered for hydronium ion production in an embodiment.

FIG. 14 Comparisons of chemical and electrochemical titrations for determination of Total Alkalinity in an embodiment.

DETAILED DESCRIPTION

Figure 1:
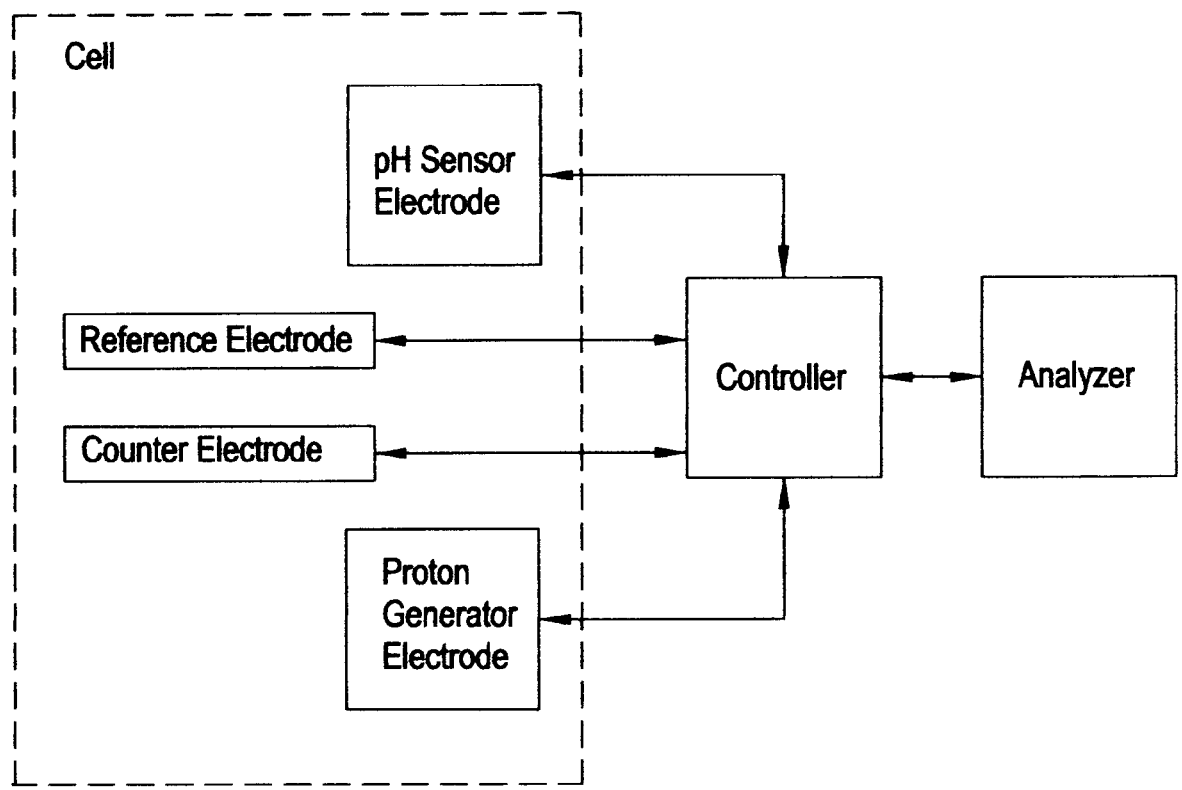
FIG. 1 illustrates a conceptual block diagram of the components of an alkalinity sensor that uses at least one boron-doped diamond electrode in an embodiment.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

This disclosure relates to the measurement of alkalinity in water. In some embodiments, this disclosure relates to accurately determining the concentration of alkalinity in a water sample with an electrochemical-based sensor employing boron-doped diamond electrodes.

An example of the traditional alkalinity titration is described in APHA (2005) Standard Methods For The Examination of Water and Wastewater, 21$^{st}$ edn. American Public Health Association, Washington, D.C. Therein is described a titration whereby the endpoint is detected by a color change of the solution.

In recent years, the manual titration process has been automated. For example, the Hach Company APA6000 analyzer provides alkalinity measurements via a sequential injection analysis method. The performance of chemical titrations with an automated instrument, however, is complicated due to a number of factors including the reagents and indicators required, the need for careful control of sample volume, close control of sequential titrant addition, endpoint recognition, and the like. However, commercial success of automated coulometric titration alkalinity sensors has been lacking, not due to lack of demand, but due to issues with performance in the field.

This application relates generally to alkalinity sensors. Alkalinity sensors herein are reagentless electrochemical devices that generate titrant in situ and monitor the change in pH of an aqueous solution over time. The pH of the solution is modified by the electrochemical generation of hydronium or hydroxide species in the sample. The electrochemical oxidation of water, for example, can generate hydronium ions (i.e., acid) for reaction with titratable bases. In the context of alkalinity determination, this is referred to as a "coulometric titration". That is, the number of electrons added or removed from the solution for the oxidation or reduction of water can be correlated to the amount of acid produced for the titration. Basic or acidic titrant is generated according to the following reactions:

Reaction 1: Electrochemical generation of base:

$$2H_2O \rightarrow 2OH^- + H_2 - 2e^- \qquad (EQN\ 1)$$

Reaction 2: Electrochemical generation of acid:

$$2H_2O \rightarrow 4H^+ + O_2 + 4e^- \qquad (EQN\ 2)$$

One design for alkalinity sensors is to use two electrode sets. The first electrode set monitors pH and the second electrode set provides the coulometric titration, which may be referred to as a hydronium generator or hydronium-generating electrode in reference to EQN 2, above. However, the reader should understand that these terms are interchangeable as the reaction may be easily reversed causing a hydronium-generating electrode to become a hydroxide ion generating electrode simply by reversing the current flow (EQN 1, above). The pH sensing electrode and the hydronium (or hydroxide) producing electrode(s) can be referred to as working electrodes. Each of the electrode sets additionally include at least a reference electrode and at least a first a counter electrode. Each set may share the same reference and counter electrodes. Each electrode set may share the same counter and have separate references or share the same reference and have separate counter electrodes. An example of a reference electrode is a Ag+/AgCl (3M KCl, saturated Ag) electrode or Saturated Calomel Electrode. The counter electrodes may be made of Pt, BDD (boron doped-diamond), carbon, or stainless steel, for example.

Embodiments disclosed herein include a method and systems for using boron-doped diamond (BDD) as the electrode material for the pH sensing and titrant-generating electrodes of an alkalinity sensor. BDD is a robust material that will work well for the pH sensing applications and for hydronium or hydroxide generation. It is capable of applying large potentials without degradation. It may be less prone to fouling than traditional electrode materials (i.e., platinum). BDD may also be less impacted by interfering currents, such as electrode oxidation, for example. It is also less electrocatalytic than platinum and gold, for instance, to redox reaction, thereby providing opportunity for less interference by other species which may be oxidized along with water. Minimizing interfering redox processes is critical for coulometric titration for alkalinity determination. In addition, plasma-based production of the BDD material allows the pH sensing and hydronium generating electrodes to be formed on the same substrate. This permits formation of a variety of electrode configurations and ease of manufacture.

FIG. 1 illustrates a conceptual block diagram of the components of an alkalinity sensor. In general, a BDD alkalinity sensor may include a pH sensor electrode and a hydronium generator made of boron-doped diamond. In addition, there may be at least one reference electrode and one counter electrode. The electrodes may be in a sample cell which may contain the aqueous solution to be analyzed. The solution may be flowing through the cell or may be static and operating in batch mode.

The two working electrodes may be located in proximity to each other within the cell to allow the hydronium generator to deliver hydronium ions to the solution that the pH electrode is monitoring. The electrodes are provided with the necessary circuitry, such as with a bipotentiostat (discussed below), so that the current and potential response at the pH sensor is indicative of the pH of the solution at the electrode surface and the current through the hydronium generator is monitored so that the amount of electrons taken from or delivered to the solution, which, for example, corresponds to the amount of hydronium ions generated, is known.

A potentiostat is an example of an electronic circuit that may be used in a controller. The potentiostat uses three electrodes to control the voltage difference across electrodes within an electrochemical cell and measure the current flow between two of three electrodes. The electrodes of a potentiostat are referred to as a reference electrode, a counter electrode, and a working electrode. In a potentiostat, the voltage between the working electrode and the reference electrode is controlled and the resulting current flow between the working electrode and the counter electrode is measured.

The alkalinity sensor will also include an analyzer that determines the alkalinity of the aqueous sample based on the coulometric titration and the resulting change in pH monitored by the pH sensor.

For simplicity, the circuitry that operates the electrodes will be referred to herein as the controller. The controller may control and monitor the hydronium or hydroxide generator to generate an amount of titrant in the aqueous sample. As discussed above, the generation of hydronium or hydroxide ions changes the pH of the aqueous sample. The controller similarly monitors the current and potential response of the pH sensor electrode for determination of the sample pH.

In one embodiment, a pair of potentiostats, one for the pH sensor and one for the hydronium generator, may be used in the circuitry of the controller. At least one of the working electrodes of each potentiostat may be a BDD electrode. In another embodiment, both of the working electrodes may be BDD electrodes. The two BDD electrodes may, or may not, be on the same substrate as described in greater detail below. The counter and reference electrodes may, or may not, be BDD electrodes.

In an alternative embodiment, a bipotentiostat, which uses a common reference electrode and counter electrode but two working electrodes could be used instead. In this embodiment, the two working electrodes are BDD electrodes. The counter and reference electrodes may, or may not, be a BDD electrode.

Figure 2:
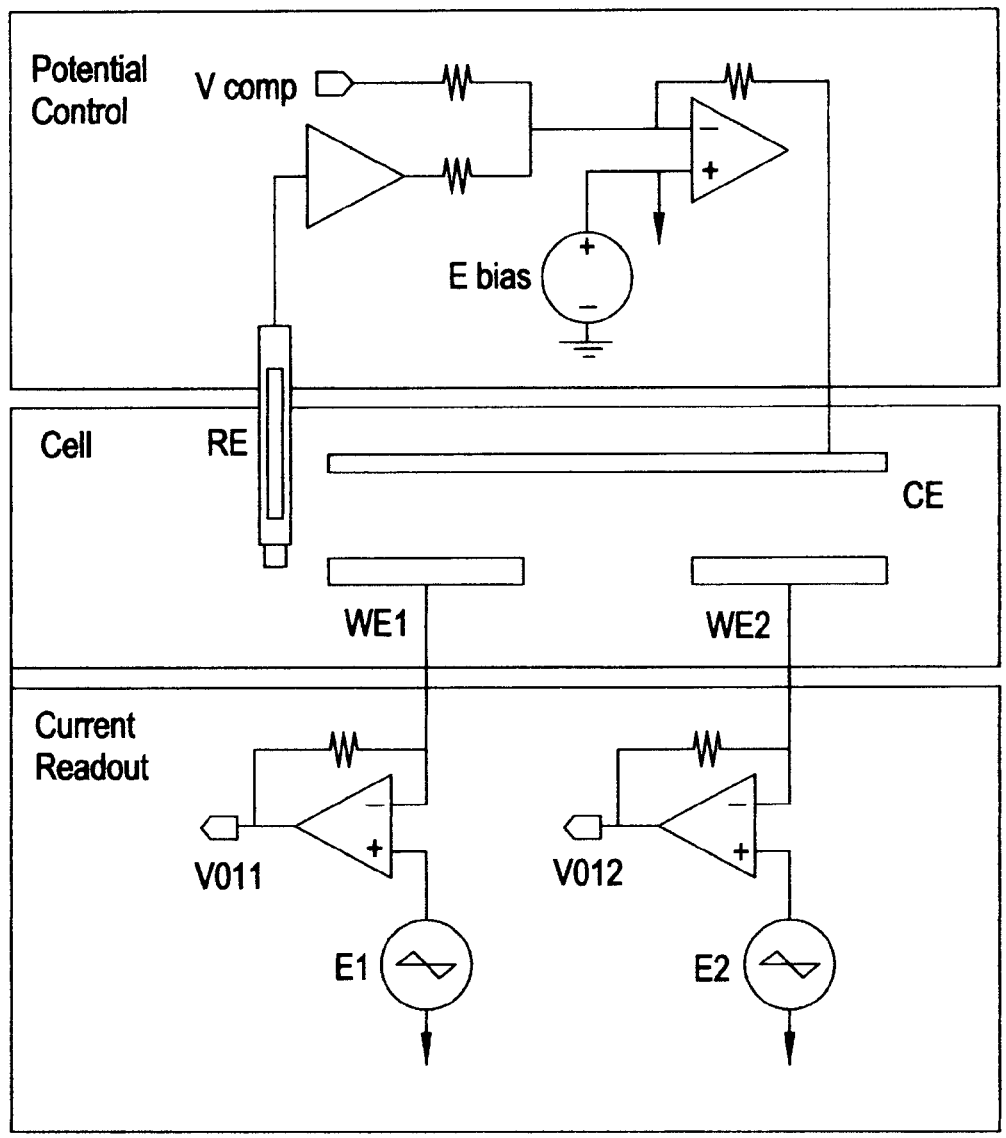
FIG. 2 illustrates a bipotentiostat suitable for use in the circuitry of a controller in an embodiment.

FIG. 2 illustrates a bipotentiostat suitable for use in the circuitry of a controller. The electrodes are referred to as a reference electrode (designated RE on FIG. 2), a counter electrode (CE), and two working electrodes (identified as WE1 and WE2). In the bipotentiostat shown, the voltage between the working electrodes and the reference electrode is controlled and the resulting current flow between the two working electrodes and the counter electrode are measured.

In an embodiment, the voltage of the working electrode is controlled, which may include applying a fixed voltage for a period of time or applying a ramped voltage in which the voltage is increased (or decreased) over time while the current for each working electrode is measured. The potential may also be applied in a pulsed or pulsed-on-a-ramped potential function (i.e., square wave voltammetry). The resulting voltage and current information is transmitted to the analyzer for determination of the sample alkalinity.

As discussed above, the pH sensor electrode, the hydronium-generating electrode or both may be made of BDD. In a particular embodiment, the hydronium-generating electrode and the pH sensor electrode are on a unitary substrate. Thus, the two working electrodes of FIG. 2 may be a single component of the alkalinity sensor that are then placed into the cell and attached to the controller circuitry during manufacture. In one embodiment, the hydronium-generating electrode and the pH sensor electrode are produced upon a substrate such as non-conducting diamond, for example.

Figure 3:
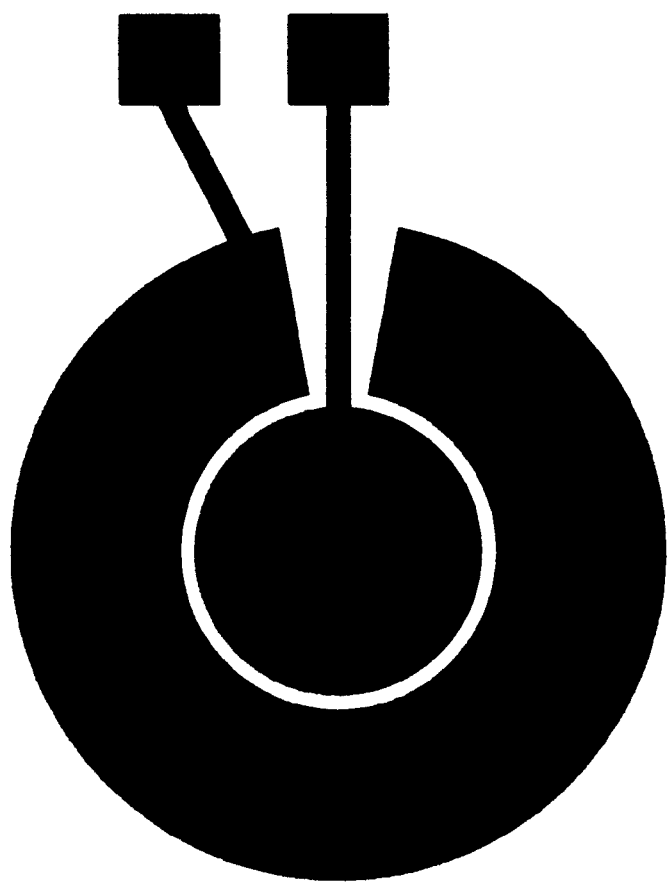
FIG. 3 illustrates a plate and ring configuration of the pH sensor electrode and the hydronium-generating electrode in an embodiment.

FIG. 3 illustrates a plate and ring configuration of the pH sensor electrode and the hydronium-generating electrode. In the embodiment shown, the pH sensor electrode is a disc of boron-doped diamond modified for the sensing of pH. The hydronium-generating electrode is a BDD ring around the pH sensor electrode.

The effects of the hydronium-generating electrode on the pH of a sample in a cell in the region near the two electrodes may be modelled. Such modelling may indicate that a pH gradient may be imposed over the entire pH sensor electrode so that the pH of the sample can be adjusted to any point as desired (P or T Alkalinity pH end points, as discussed above). Subsequently, the amount of current necessary to obtain the particular pH may then be used to determine the alkalinity of the sample.

FIGS. 4A-4I illustrates several other pH sensor and hydronium-generating electrode configurations that may be easily obtained by BDD on a unified substrate. In the various embodiments illustrated, the pH sensor electrode is illustrated with a diagonal line fill and the hydronium-generating electrodes are illustrated with a horizontal line fill. FIG. 4A illustrates a simple embodiment of two electrodes side by side. FIG. 4B shows a pH sensor electrode between two hydronium-generating electrodes. This embodiment may be reversed to have two pH sensor electrodes surrounding a hydronium-generating electrode, also. FIG. 4C illustrates a series of alternating electrodes which may be particularly suitable to a flow-through cell. FIG. 4D illustrates an embodiment in which a U-shaped hydronium-generating electrode surrounding a square pH sensor electrode. FIG. 4E illustrates a rectangular pH sensor almost entirely surrounded by a hydronium-generating electrode. Embodiments 4A-4E are suitable for configurations in which the electrodes are connected by surface leads, illustrated by the darker lines, to the controller.

Embodiments 4F-4I are suitable for embodiments in which the electrodes are connected from below, such as through vias in the substrate, or above by attached wires. FIG. 4F illustrates a circular ring pH sensor electrode that completely surrounds a circular hydronium generator. FIG. 4G illustrates a hexagonal version of FIG. 4F. FIG. 4H illustrates the embodiment of FIG. 4F with an additional hexagonal hydronium-generating electrode within the pH sensor electrode. FIG. 4I illustrates a square hydronium-generating electrode surrounding a disc-shaped pH sensor electrode. Other similar electrode configurations may be used and the disclosed configurations are not exhaustive.

In addition to the two-dimensional configurations provided above, 3-dimensional (3D) pH sensor and hydronium-generating electrode configurations may be possible. In a simple embodiment, each electrode may be a plate and the two electrodes may be adjacent to each other with the solution to be analyzed between the plates. In yet another 3d configuration, two hydronium-generating plates may be provided, and may be wired in series to act as a single electrode or may be operated separately, and the pH sensor electrode may be placed between them. Many other electrode configurations are possible.

Figure 5:
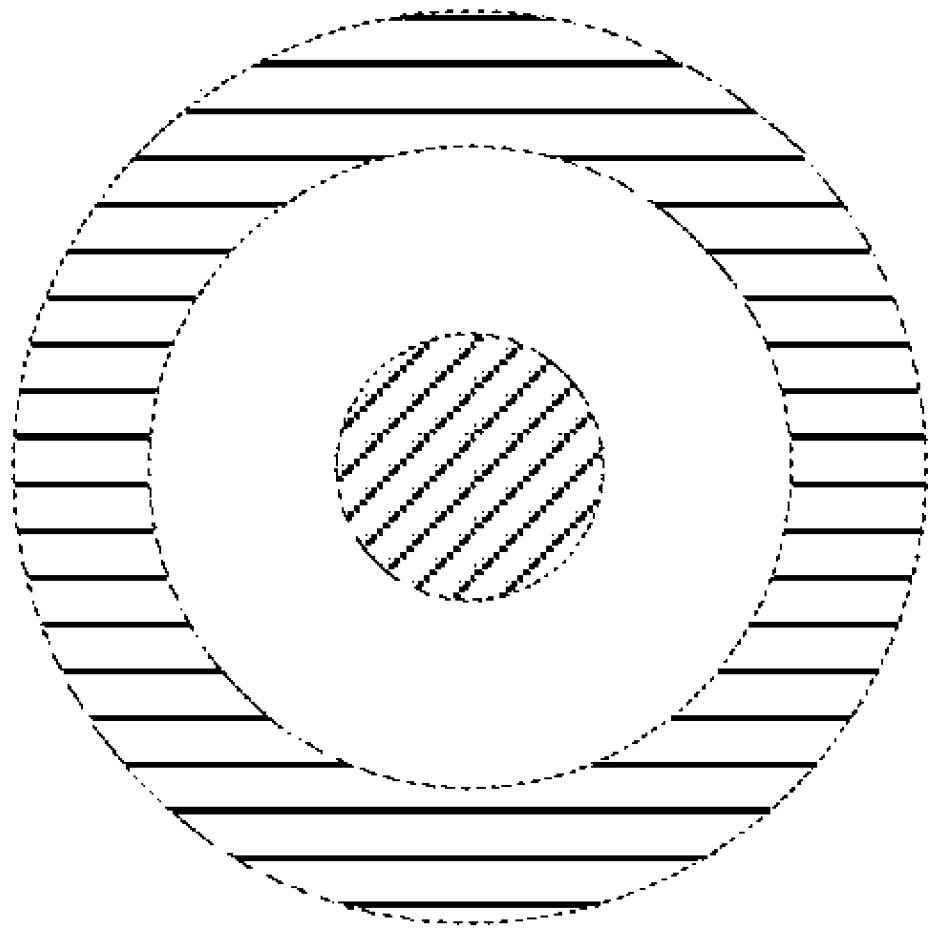
FIG. 5 illustrates a cross section of a 3d electrode configuration in which the pH sensor is a rod of BDD within a shell of BDD that acts as the hydronium-generating electrode in an embodiment.

FIG. 5 illustrates a cross section of a 3D electrode configuration in which the pH sensor is a rod of BDD within a shell of BDD that acts as the hydronium-generating electrode. The analyte solution may flow through the annulus between the two electrodes.

Figure 6:
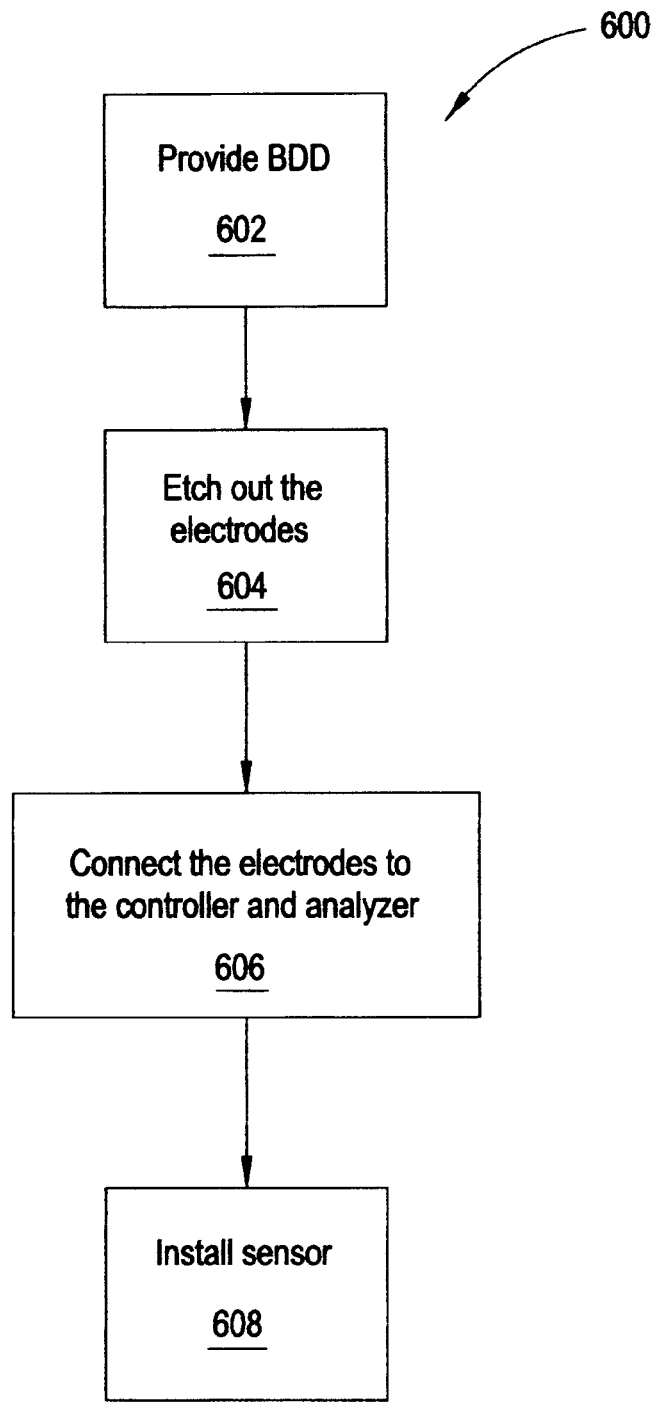
FIG. 6 illustrates a method of manufacturing the electrodes for a BDD alkalinity sensor in an embodiment.

FIG. 6 illustrates a method of manufacturing the electrodes for a BDD (boron-doped diamond) alkalinity sensor. In the method 600, a substrate with a layer of BDD is provided in a providing operation 602. Then, at least a portion of the BDD layer is removed to create a first portion of BDD separated from a second portion of BDD in a removing operation 604. For example, the portions may be shaped as shown in FIGS. 4A-4I. The removing operation 604 may involve lapping, chemical etching, laser cutting or any other suitable technique.

The two portions are then connected to the circuitry of the alkalinity sensor to act as the pH sensor electrode and hydronium-generating sensor, respectively, in an electrode connecting operation 606. The sensor may then be installed in a cell in an installation operation 608.

While not limited to this type of embodiment, analysis may be easier in a static cell that has no flow. In one embodiment, a sensor may be provided with a cell that has a known volume and is well mixed during analysis. While this may take more time, if the entire cell is well mixed and allowed to completely reach equilibrium of pH throughout the entire sample, all dynamic effects may be eliminated and a precise measurement of alkalinity may be obtained. In yet another configuration, a single cell may be provided with multiple sensors and the results of each sensor may be used to determine a more accurate alkalinity.

A portable sensor embodiment may be created. In such an embodiment, a cell may be defined by an enclosure around the electrodes which defines a sample volume. The enclosure allows sample into the cell, isolates it from the bulk sample during measurement and allows entrapped sample out and new sample in to the enclosure. By characterizing the configuration, the analyzer may be calibrated so that the portable sensor need only be inserted into flowing or quiescent analyte solution for a period of time to obtain an alkalinity measurement.

FIG. 7 shows the electrochemical cell used to determine the alkalinity in this invention. There are two major compartments in this cell. The first compartment contains the BDD electrode for generating hydronium ions and the BDD electrode for measuring pH. This compartment is where the sample to be analyzed is held and the electrochemical titration is performed. A conductive material like brass may be present underneath the BDD hydronium ion generator to provide electrical contact to the BDD electrode. An electrochemical workstation (Meter Electronics Controller/Recorder) may be used to apply the necessary current or voltage for generating hydronium ions. The same workstation may also be used to measure the pH. A switch may be used to alternate between the BDD hydronium ion generator and the BDD-based pH sensor. A peristaltic pump may deliver the fluid to the compartment where the electrochemical analysis is performed. All measurements are performed with a quiescent sample. A second compartment contains the reference (e.g., $Ag^+/AgCl$) and counter electrodes (e.g., platinum) in a reservoir that is connected by solution via a conduit to the working electrode compartment. Spatial separation of these two compartments is required so that the hydronium ions generated at the BDD hydronium ion generator do not interact with species generated at the counter electrode. The outlet of the sample is in the second compartment, where after analyses, the sample exits out.

Figure 8:
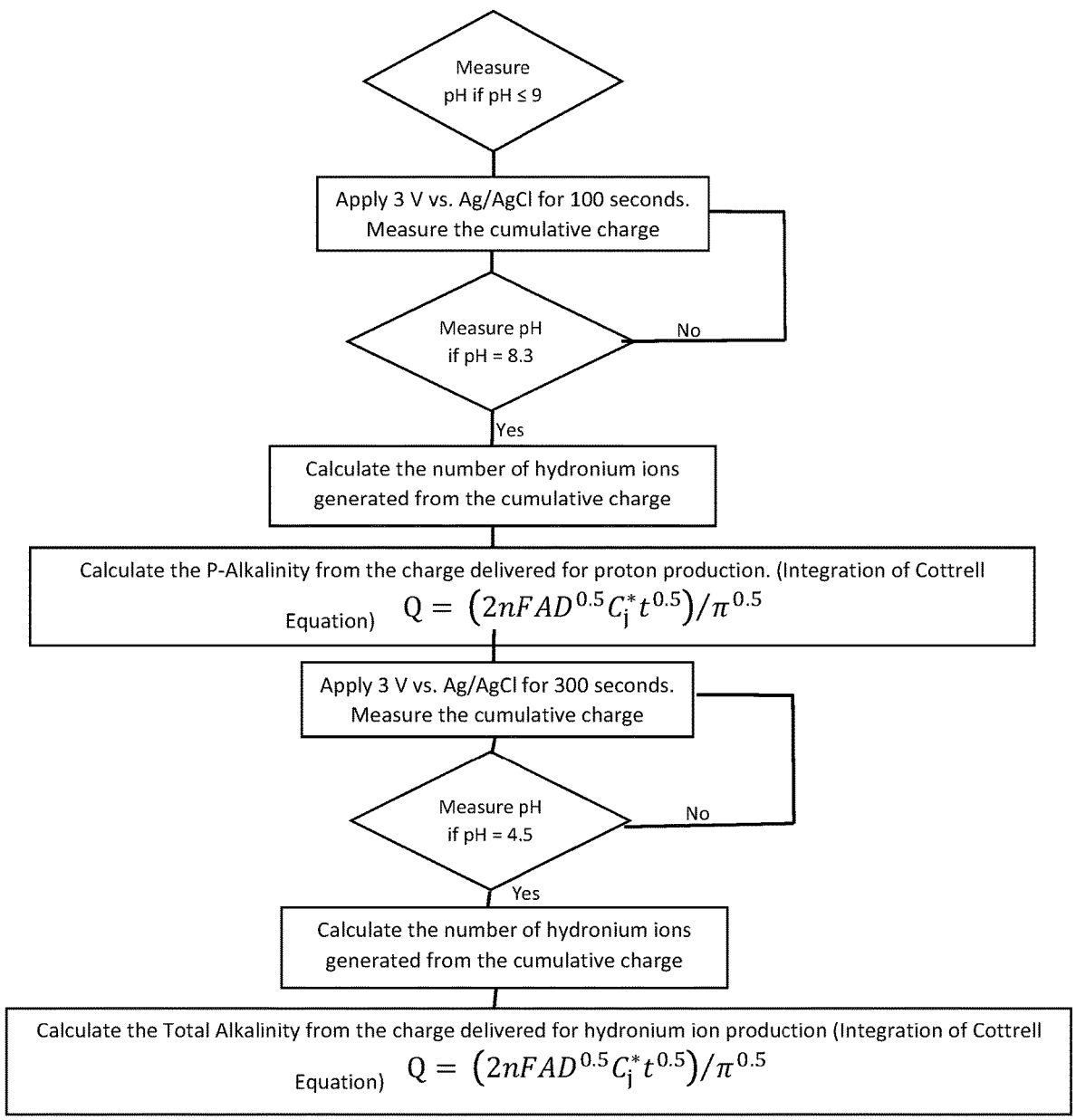
FIG. 8 is a block diagram showing a process of electrochemical generation of hydronium ions and subsequent measurement of pH using BDD electrodes in the alkalinity cell for determination of P-Alkalinity and T-Alkalinity of a sample in an embodiment.

FIG. 8 shows a block diagram for the measurement of P- and T-Alkalinity. The sample is delivered to the first compartment and held in the reaction chamber for analysis via a stopped-flow or batch process. The pH is measured at the start of the experiment by the BDD pH sensor. If the pH is less than 8.3, then there is no P-Alkalinity. The hydronium ion generator is turned on by applying a constant current or voltage. The current-time profile is recorded and the current is integrated with respect to time to obtain the charge. Using the total charge delivered the number of hydronium ions delivered is determined by integrating the Cottrell equation. The number of hydronium ions consumed to reduce the sample pH to 4.5 is used to calculate the Total Alkalinity of the sample. If the pH is greater than 8.3 then the hydronium ions produced to reduce the sample pH to 8.3 corresponds to the P-Alkalinity FIG. 9 illustrates a typical current-time profile during hydronium ion generation for a sample containing ~600 mg/L alkalinity as $CaCO_3$. The asymptotic decay of the current is due to the diffusion limited process that is occurring at the electrode wherein the hydronium ion production gradually decreases because of the concentration gradient formed at the interface of the electrode. The integration of the current with respect to time provides the cumulative charge. Using the integrated Cottrell equation one can find the amount of hydronium ions produced in the system. The integrated Cottrell equation is as follows:

$$Q=(2nFAD^{0.5}C_j*t^{0.5})/\pi^{0.5}$$ (Integration of Cottrell's Equation)

where n is the number of electrons transferred during the hydronium ion production, F is Faraday's constant, A is the area of the electrode, D is the diffusion coefficient of protons. The diffusion coefficient is a function of temperature, is the concentration of hydronium ions produced at any given time during the experiment, and t is the time of the experiment. The initial pH of the sample solution also impacts the electrochemical hydronium generation.

Figure 10:
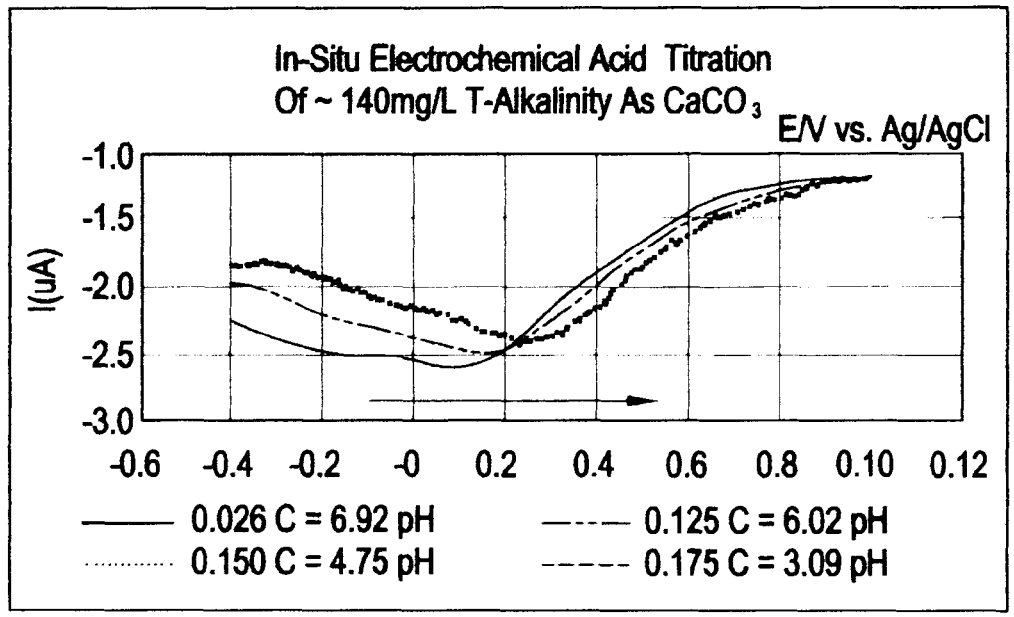
FIG. 10 shows square wave voltammograms obtained for pH determination by a BDD-based pH sensor during the generation of hydronium ions to neutralize the buffer capacity for an in situ electrochemical titration to determine sample alkalinity in an embodiment.

FIG. 10 shows square wave voltammograms generated in the measurement of pH after several in situ hydronium ion generation steps. A positive potential shift in the peak current potential indicates the pH decreased with the increase of charge passed at the BDD hydronium generating electrode. This decrease in pH corresponds to the neutralization of the buffer capacity of the system. This decrease in pH demonstrates the ability of this method and the cell to produce hydronium ions and measure the pH to determine sample alkalinity without the need for any reagents as required in common chemical titrations. The alkalinity of the sample as measured through standard titrations was ~140 mg/L Total Alkalinity as $CaCO_3$. Monohydrogen and dihydrogen phosphates were responsible for the alkalinity of the sample.

Figure 11:
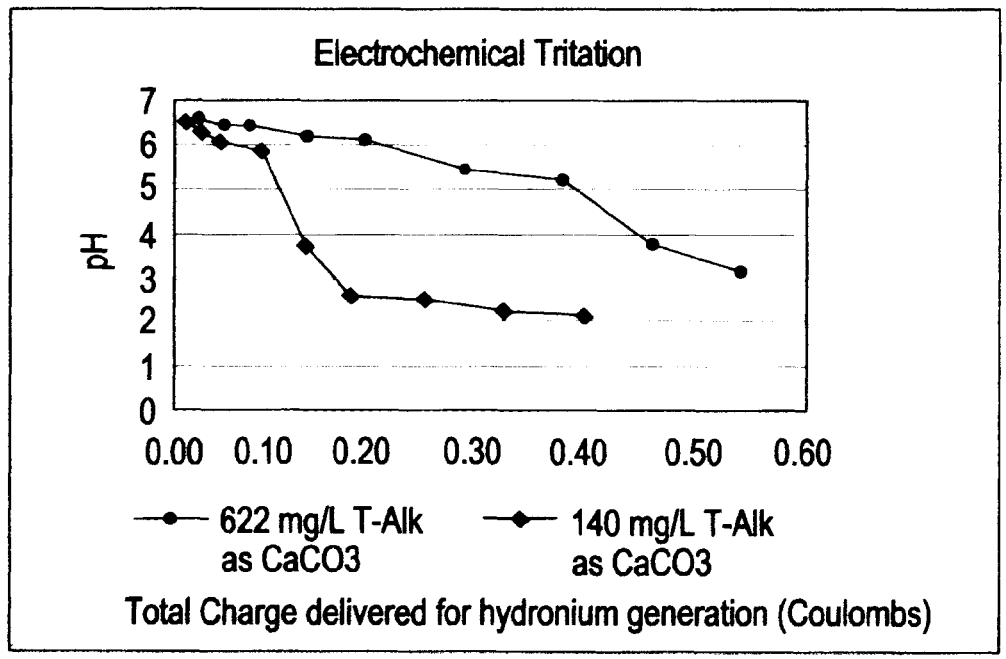
FIG. 11 Electrochemical titration of 622 mg/L and 140 mg/L Total Alkalinity (as $CaCO_3$) in an embodiment.

FIG. 11 shows titration curves generated using the electrochemical titration method and the cell described in FIGS. 7 & 8. It is evident from FIG. 11 that the endpoint for a lower alkalinity sample (140 mg/L) occurs at a lower charge than the higher alkalinity (622 mg/L). This demonstrates that there is a functional relationship between the alkalinity of the sample and the charge delivered into the system during the electrochemical proton generation. The ability to measure the pH before, during and after the hydronium ion generation with a small cell volume (e.g., ~30-50 uL) enables effective reagentless measurement of alkalinity.

Figure 12:
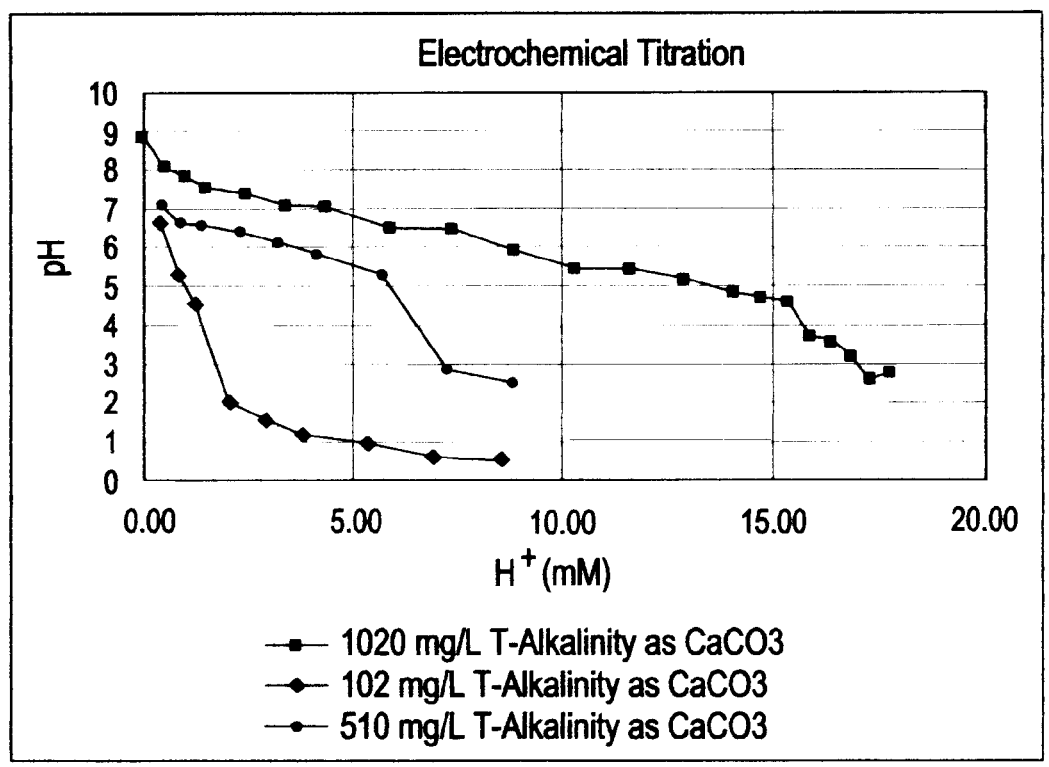
FIG. 12 show plots for quantification of the hydronium ions consumed during electrochemical titrations for determination of Total Alkalinity in an embodiment.

FIG. 12 shows the electrochemical titration of three different alkalinity samples. The alkalinity in the samples tested here is due to hydroxides and carbonates and not phosphate (described in FIG. 10). The functional dependence of the hydronium ions generated at the BDD hydronium ion generating electrode and measured the BDD-based pH sensor is evident from the graph. FIGS. 11 & 12 show that this alkalinity sensor is capable of measuring total alkalinity due to phosphate, hydroxides and carbonates.

Figure 13:
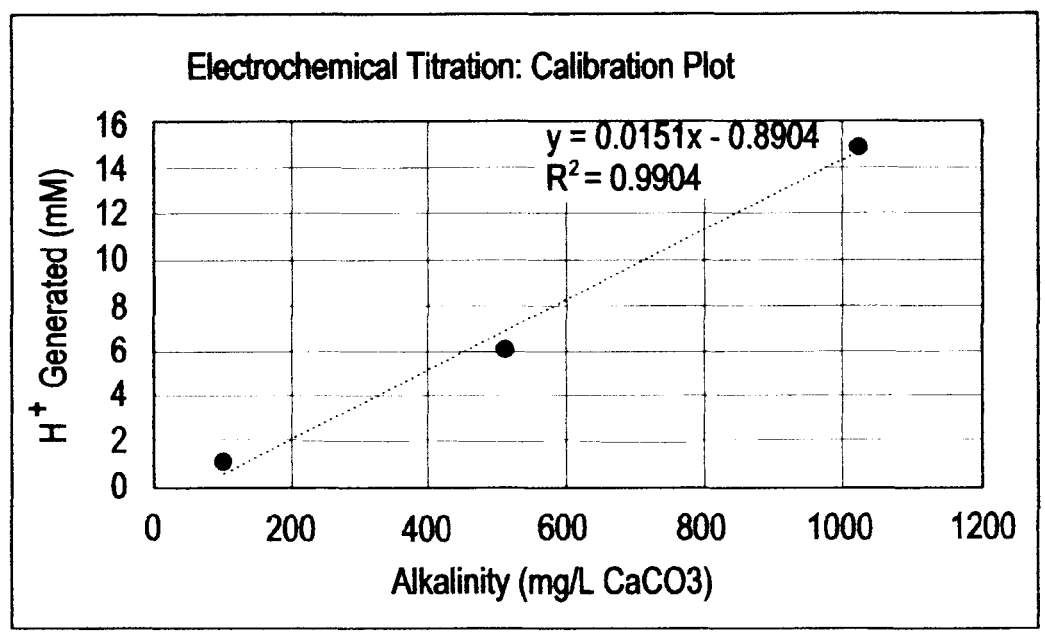
FIG. 13 Calibration plot generated through electrochemical titration of ~100-1000 mg/L as $CaCO_3$ Total alkalinity samples in an embodiment.

FIG. 13 shows a calibration plot generated using the electrochemical titration procedure. The end point at pH 4.5 (for the measurement of Total Alkalinity) has a linear relationship with the number of hydronium ions generated at the BDD hydronium ion generating electrode. A linear relationship with an $R^2$-value of 0.99 was obtained for a Total Alkalinity range of ~100-1000 mg/L as $CaCO_3$. This calibration plot may be used to determine the Total Alkalinity of an unknown sample.

FIG. 14 shows the comparison of electrochemical titrations employing the BDD-based system described herein and chemical titrations. The hydronium ion consumption for neutralizing the same buffer capacity appears lower for the electrochemical process when compared to the chemical process. The electrochemical titrations closely track the chemical titrations. As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as a system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for determining the alkalinity of an aqueous sample using an alkalinity sensor, comprising:
   monitoring the pH of an aqueous sample using a pH sensor in a sample cell, the pH sensor including a pH sensor electrode made of boron-doped diamond;
   controlling, using a peristaltic pump, a flow of the aqueous sample between the pH sensor and a boron-doped diamond hydronium generator, wherein the pH sensor and the boron-doped diamond hydronium generator each form a portion of a lumen to form a path for the flow of the aqueous sample;
   generating hydronium ions, using the boron-doped diamond hydronium generator, in the aqueous sample in the sample cell, the boron-doped diamond hydronium generator including a boron-doped diamond hydronium-generating electrode, wherein the alkalinity sensor comprises at least one counter electrode and at least one reference electrode separated from the sample cell by a restrictive conduit, wherein the at least one counter electrode and the at least one reference electrode are placed at a position relative to the aqueous sample from the group consisting of: fore and aft;

changing the pH of the aqueous sample by causing the boron-doped diamond hydronium generator to generate a number of hydronium ions in the aqueous sample;

quantifying and converting a current or charge to the number of hydronium ions produced to an end point of an electrochemical titration, the end point correlating to the alkalinity of the aqueous sample; and analyzing the alkalinity of the aqueous sample based on the quantified number of hydronium ions and the resulting change in pH monitored by the pH sensor.

2. The method of claim 1, wherein the hydronium-generating electrode and the pH sensor electrode are on a unitary substrate.

3. The method of claim 1, wherein the hydronium-generating electrode and the pH sensor electrode comprise boron-doped diamond on a single substrate.

4. The method of claim 1, wherein the pH sensor electrode comprises a disc of boron-doped diamond and the hydronium-generating electrode comprises a plate spaced apart from the pH sensor.

5. The method of claim 1, wherein the pH sensor electrode comprises a disc of boron-doped diamond and the hydronium-generating electrode comprises an open ring surrounding the pH sensor.

6. The method of claim 1, wherein the pH sensor electrode comprises a first plate of boron-doped diamond and the hydronium-generating electrode comprises a second plate of boron-doped diamond spaced apart from the first plate.

7. The method of claim 1, wherein the hydronium-generating electrode comprises a plate having an aperture and the pH sensor electrode is located within the aperture.

8. The method of claim 1, wherein the boron-doped diamond hydronium generator has more than one hydronium-generating electrode.

9. The method of claim 1, wherein the pH sensor electrode, the boron-doped diamond hydronium generator and a controller are part of a potentiostat and wherein the pH sensor electrode is a first working electrode of a bipotentiostat and the hydronium generating electrode is a second working electrode of the bipotentiostat.

* * * * *